United States Patent [19]
Ikeda

[11] Patent Number: 5,270,218
[45] Date of Patent: Dec. 14, 1993

[54] ANALYTICAL METHOD AND APPARATUS FOR ANALYZING SUBSTANCES

[75] Inventor: Makoto Ikeda, Ichihara, Japan

[73] Assignee: Idemitsu Kosan Co., Ltd., Tokyo, Japan

[21] Appl. No.: 653,951

[22] Filed: Feb. 12, 1991

Related U.S. Application Data

[63] Continuation of Ser. No. 532,674, Jun. 4, 1990, abandoned, which is a continuation of Ser. No. 259,930, Oct. 19, 1988, abandoned.

[30] Foreign Application Priority Data

Oct. 30, 1987 [JP] Japan .................. 62-273417

[51] Int. Cl.$^5$ .............................. G01N 25/14
[52] U.S. Cl. ...................... 436/148; 422/67; 422/68.1; 422/81; 436/158; 436/181
[58] Field of Search .............. 422/68.1, 81, 67; 436/147, 148, 158, 181

[56] References Cited

U.S. PATENT DOCUMENTS

| | | | |
|---|---|---|---|
| 3,927,978 | 12/1975 | Wasik | 436/143 |
| 4,253,845 | 3/1981 | Smernoff | 422/99 |
| 4,670,400 | 6/1987 | Leenders et al. | 436/34 |
| 4,671,298 | 6/1987 | Babb et al. | 436/132 |

OTHER PUBLICATIONS

Poole, et al., *J. High Resolution Chrom. & Chrom. Comm.*, vol. 6, Oct. 1983, pp. 537-539.
Karasek, et al., *Anal. Chem.* (1984) vol. 56 p. 192R.
Walas, *Phase Equilibria in Chemical Engineering*, Butterworth Publishers, Boston (1985) pp. 534-535.

*Primary Examiner*—Jill A. Johnston
*Attorney, Agent, or Firm*—Antonelli, Terry, Stout & Kraus

[57] ABSTRACT

An analytical method which comprises sampling a predetermined amount of a liquid sample, bringing the sample to a vapor-liquid equilibrium at a predetermined temperature and pressure, separating the resultant gaseous and liquid fractions from each other, and analyzing the gaseous fraction as a gas sample and the liquid fraction as a liquid sample, and an apparatus for practicing the analytical method. By this method or apparatus, the light and heavy fractions of a substance can be simultaneously analyzed in composition and chemical structure. This enables the modification and the service life of a chemical substance like a lubricating oil, in which the qualities may change with the passage of time, to be estimated or foreseen.

3 Claims, 2 Drawing Sheets

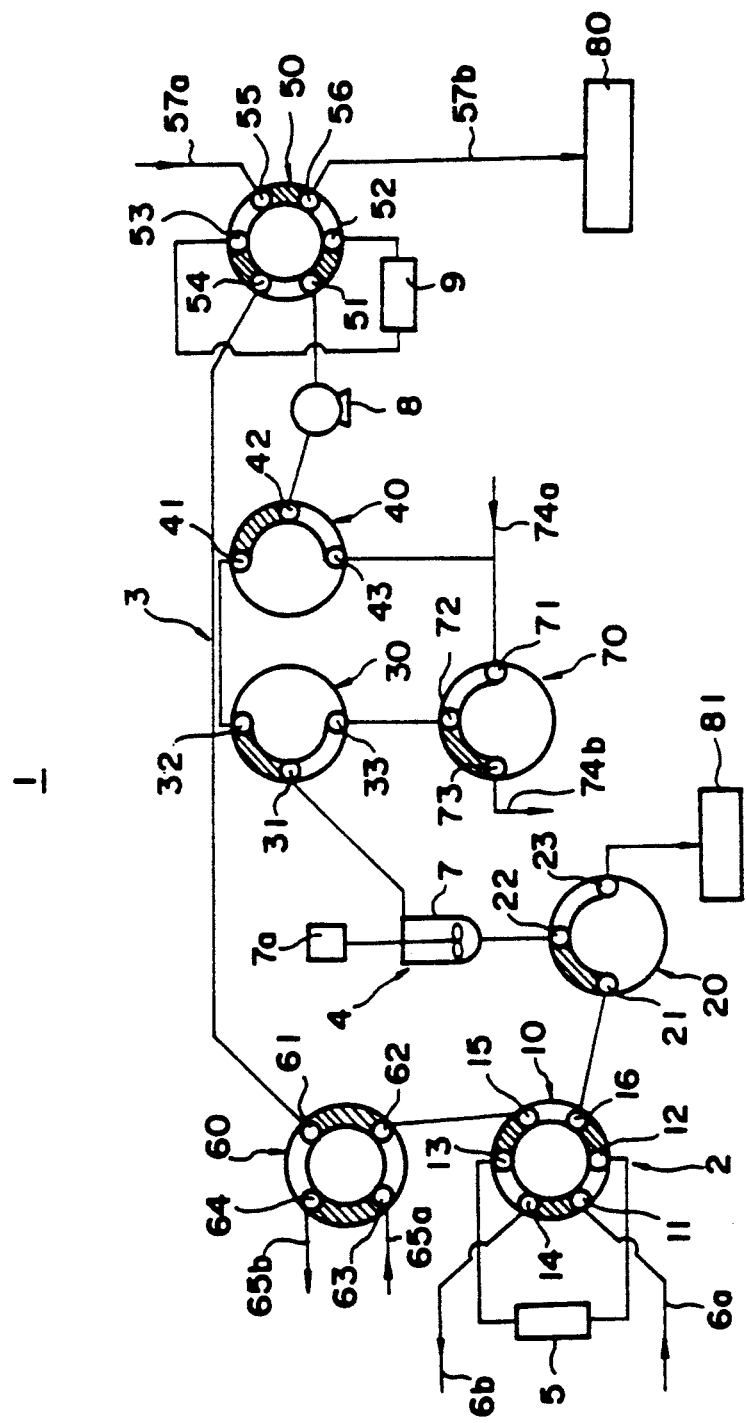
FIG. I

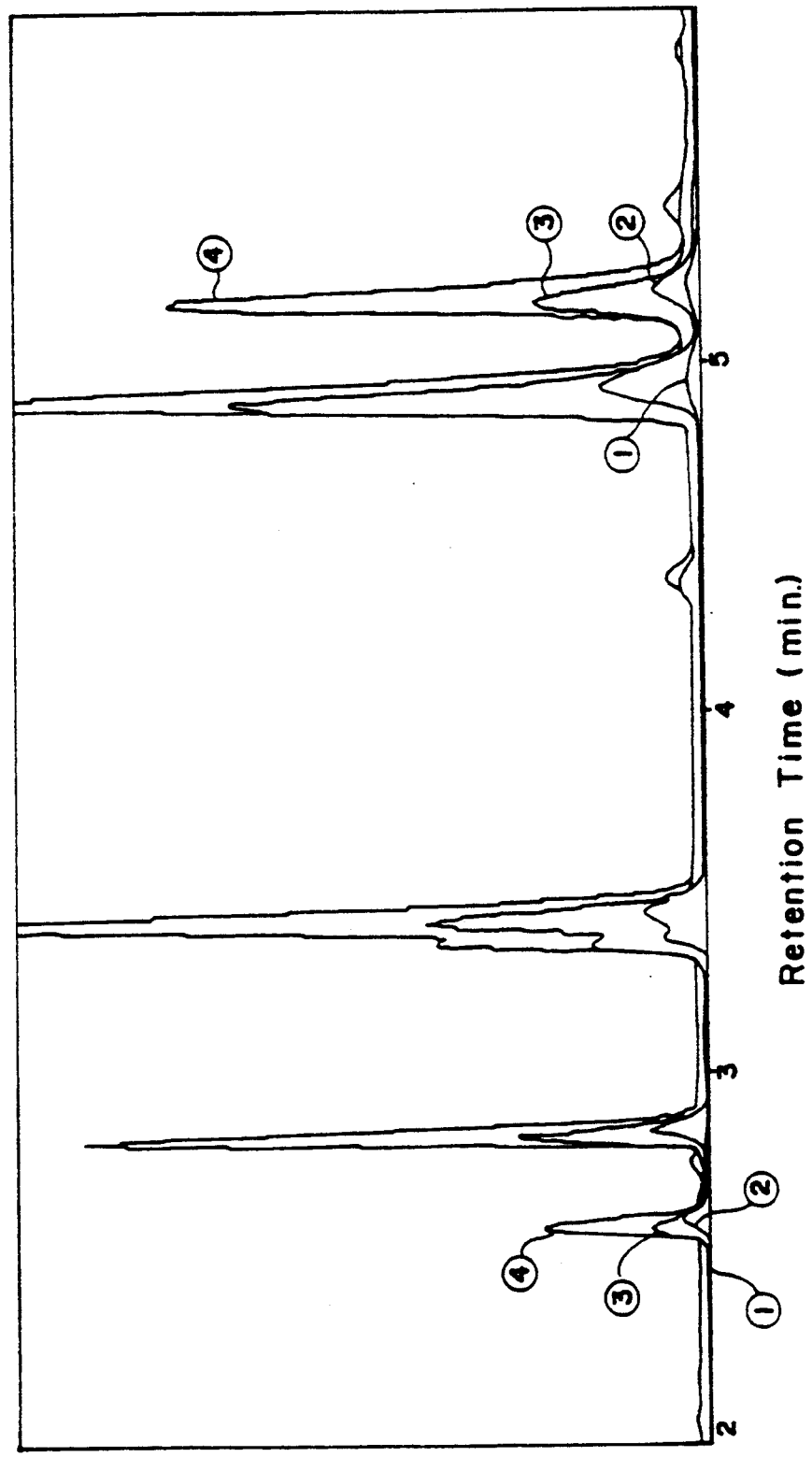

ANALYTICAL METHOD AND APPARATUS FOR ANALYZING SUBSTANCES

This is a continuation of application Ser. No. 532,674, filed Jun. 4, 1990 (now abandoned), which is a continuation of application Ser. No. 259,930, filed Oct. 19, 1988 (now abandoned).

BACKGROUND OF THE INVENTION

1. Field of the Invention

This invention relates to an analytical method and apparatus for analyzing substances, and more particularly to an analytical method and apparatus for analyzing substances such as a liquid substance like lubricating oil, the qualities of which may change as the time proceeds, whereby the modification or service life of the substance can be estimated or foreseen simply and precisely.

2. Description of the Related Art

Conventionally, for estimating or foreseeing the modification and service life of chemical substances the qualities of which may change as the time proceeds, like lubricating oils during use, fats and oils during storage, and so on, various chemical and physical analytical methods have been employed to measure the neutralization values and the viscosities of the substances.

Although the conventional methods are useful to know whether chemical substances have been modified, degraded or not, they have no effect for estimating or foreseeing the service life of the chemical substances.

In like manner, though infrared spectrography, gas chromatography, and the like are useful to elucidate the chemical structures of chemical substances, they are inefficient in estimating and foreseeing the modification and the service life of chemical substances. Moreover, it is impossible to analyze both of the light and heavy fractions of a chemical substance using only these analytical methods.

In brief, by any of the conventional analytical methods, it is very difficult to estimate and foresee the modification and the service life of a chemical substances in which the qualities may change with the passage of time, though it is generally recognized to be of great importance.

In view of the foregoing, the inventor has intensively studied to develop an analytical method and apparatus for analyzing a substance which, by surpassing the above-mentioned disadvantages of conventional analytical methods, realize the foreseeing or quickly recognizing the modification and service life of a liquid chemical substance such as a lubricating oil, etc.; in which the qualities may change with the passage of time. As a result of the extensive study, it has been found that the foreseeing or quickly recognizing as described above is facilitated by separating the liquid chemical substance at the proper temperature and pressure into light and heavy fractions, namely vapor and liquid fractions, and analyzing both of the fractions simultaneously.

SUMMARY OF THE INVENTION

The present invention relates to an analytical method for analyzing substances which comprises sampling a predetermined amount of a liquid sample, bringing the sample to a vapor-liquid equilibrium at a predetermined temperature and pressure, separating the gaseous and liquid fractions from each other, and analyzing the gaseous fraction as a gas sample and the liquid fraction as a liquid sample.

The present invention relates also to an analytical apparatus comprising a sampling portion or section in which a predetermined amount of a liquid sample is collected, a vapor-liquid equilibrium portion or section which the sample is brought to a vapor-liquid equilibrium under conditions of temperature and pressure controlled to predetermined values, and a vapor-liquid separation portion in which the gaseous and liquid fractions produced in the vapor-liquid equilibrium portion are separated from each other.

BRIEF DESCRIPTION OF THE DRAWINGS

FIG. 1 is a system diagram of an analytical apparatus of the invention; and

FIG. 2 is a graph illustrating gas chromatographic analytical results obtained according to the invention.

In FIG. 1, an analytical apparatus is denoted by the reference number 1; a sampling portion, by reference numeral 2; a vapor-liquid equilibrium portion by reference numeral 3; a vapor-liquid separation portion by reference numeral 4; a sampling column by reference numeral 5, a vapor-liquid separation vessel by reference numeral 7; a gas sampling column by reference numeral 9, six-way valves by 10, 50; cross valves by reference numeral 20, 30, 40, and 70; a gas analytical apparatus by reference numeral 80; and liquid analytical apparatus by reference numeral 81.

DESCRIPTION OF PREFERRED EMBODIMENT

Hereinafter, the present invention will be described, making reference to FIG. 1. The analytical method of the invention may be carried out by using various techniques. Preferably, the present analytical method is most efficiently and precisely conducted with the present apparatus for analyzing substances.

In FIG. 1, the analytical apparatus 1 consists of a sampling portion 2 in which a predetermined amount of a sample is collected, a vapor-liquid equilibrium portion 3 in which the sample is brought to a vapor-liquid equilibrium by heating to a predetermined temperature and controlling pressure to a predetermined value, and a vapor-liquid separation portion 4 in which the gaseous and liquid fractions of the sample produced in the vapor-liquid equilibrium portion 3 are separated from each other. Each portion is placed in a constant temperature air bath, in which the temperature is controlled at a predetermined levels in relationship to each action of the portions.

The sampling portion 2 is consists of a six-way valve 10, a sampling column 5, a sample introduction pipe 6a, and a sample discharge pipe 6b. The vapor-liquid equilibrium portion 3 is consists of a closed flow-path having the vapor-liquid separation vessel 7 of the vapor-liquid equilibrium portion 4 incorporated therein. More particularly, the closed flow-path is constituted by the above-described six-way valve 10, a cross valve 20, a vapor-liquid separation vessel 7, a cross valve 30, a cross valve 40, circulation pump 8, a six-way valve 50, a gas sampling column 9, a four-way valve 60, and a piping for connecting the valves and so forth.

The above-described four-way valves 60 is provided with pipings 65a and 65b for introducing or discharging a solvent for diluting the sample. The analytical apparatus 1 is provided with a cross valve 70, pipings 74a, 74b for introducing and discharging a purge gas to maintain the interior of analytical apparatus 1 at a standard state, and to clean or dry the interior of the apparatus 1. The six-way valve 50 is provided with pipings 57a, 57b for introducing and discharging a carrier gas into and out of the closed flow-path.

The analytical apparatus 1 of the invention, which has such a constitution as described above, is applied to the analysis of a sample by operating the valves in the following order.

First, the valves and pipings within analytical apparatus 1 are brought to a predetermined temperature. In this state, the six-way valve 10 is switched to the sampling side so that a sample is delivered into the sampling column 5. More particularly, the sample flows through the sample introduction pipe 6a, valve opening 11, valve opening 12, sampling column 5, valve opening 13, valve opening 14, and sample discharge pipe 6b in that order. As a result, a predetermined amount of the sample flows into the sampling column 5.

With these valves operating, circulation pump 8 is operated so that the sample is circulated with purge gas adjusted to a predetermined pressure through the closed flow-path in the vapor-liquid equilibrium portion. More particularly, the purge gas is circulated from circulation pump 8, through valve opening 51, valve opening 52, gas sampling column 9, valve opening 53, valve opening 54, valve opening 61, valve opening 62, valve opening 15, valve opening 13, sampling column 5, valve opening 12, valve opening 16, valve opening 21, valve opening 22, vapor-liquid separation vessel 7, valve opening 31, valve opening 32, valve opening 41, valve opening 42, and to circulation pump 8. The sample is fed with and subjected to bubbling with purge gas in vapor-liquid separation vessel 7 to produce a gaseous fraction, which is circulated through the closed flow-path from vapor-liquid separation vessel 7. But, the liquid fraction of the sample remains in the vapor-liquid separation vessel 7.

After a predetermined period of time, circulation is stopped. Then, carrier gas is made to flow through valve opening 55, valve opening 53, gas sampling column 9, valve opening 52, and valve opening 56, so that the gaseous fraction is fed into a gas analytical apparatus such as a gas chromatograph, and so on.

A dilution solvent supplied from piping 65a is introduced into the vapor-liquid separation vessel 7 via valve opening 63, valve opening 62, valve opening 15, valve opening 13, sampling column 5, valve opening 12, valve opening 16, valve opening 21, and valve opening 22, which dilutes the liquid fraction. The diluted liquid fraction is then fed to an apparatus for analyzing liquids 81 such as a liquid chromatograph, and so forth through valve opening 22 and valve opening 23.

As seen from the above description, the analytical apparatus 1 has such a constitution that the switching of each valve, the operation of the pump, the supply of a carrier gas and dilution solvent can be regulated on a definite schedule. This facilitates analysis in which a predetermined amount of a sample is allowed to come to a vapor-liquid equilibrium at predetermined temperature and pressure, and is separated into gaseous and liquid fractions, as gas and liquid analytical samples. Moreover, each operation can be automated, which enhances the reproducibility and reliability of analytical results.

Regarding the gas and liquid analytical apparatus for the invention, analytical apparatus generally used for such purposes may be properly selected, according to the type of liquid and gaseous samples to be analyzed.

Typical gas analytical apparatus such as a gas chromatograph-mass spectrometer and the like are exemplified in addition to the above-described gas chromatograph. Liquid analytical apparatus such as an infrared spectroscope, ultra-violet and visible ray spectroscopes, and so forth may be properly selected, depending on the type of samples.

To prepare the next sample, in analytical apparatus 1 after sampling, a purge gas such as nitrogen gas, helium gas, or the like is introduced through piping 74a via valve opening 43. It is made to flow through each valve and pipe in the closed flow-path, and is discharged through piping 74b via valve openings 72 and 73 to dry the interior of the valves and the pipes.

As described above, according to the present invention, a sample is separated into gaseous and liquid fractions which are analyzed respectively. This enables the light and heavy fractions of a substance to be simultaneously analyzed in composition and chemical structure. Moreover, the modification and the service life of a chemical substance such as a lubricating oil in which the qualities may change with the passage of time can be estimated or foreseen. The present analytical method and apparatus for analyzing a substance are of high practical usefulness, and are expected to be used in diversified fields.

The invention will be more clearly understood with reference to the following example.

EXAMPLE

The samples used for the analysis were a lubricating oil (sample ①) having a viscosity of 400 cSt. at 40° C. and a total acid value of 0.1 mg KOH/g, and samples (sample ②, ③, and ④, respectively) prepared by pyrolysis of the sample ① at high temperature for 24 hours, 120 hours and 240 hours. For pyrolysis at high temperature, water equal to 5% by weight was added to the samples which were then heated at 300° C. in an autoclave, and pressurized at 15 kg/cm².

The separation of each sample was conducted at 60° C. and 0 kg/cm² in pressure (gauge pressure) by using helium gas as a carrier gas. The obtained gaseous fraction was analyzed with a gas chromatograph, and the liquid fraction with a liquid chromatograph.

FIG. 2 illustrates the analytical results of the gaseous fraction of each sample. The peaks exhibited sequentially from left to right in each chromatogram were due to methane, ethane, propane, isobutene, isobutane and n-butane, respectively. The peaks of the sample ④ were higher than those of the sample ①. This revealed that the amount of the light fractions such as methane, ethane and the like increased as pyrolysis at a high temperature was prolonged.

The analytical results of the liquid fractions were as follows: The results described below are relative molecular weights based on 100 being the molecular weight of the liquid fraction of sample ①.

Sample ①: 100
Sample ②: 90
Sample ③: 87
Sample ④: 82

The analytical result revealed that the molecular weight the samples decreased as high temperature pyrolysis time was longer.

Based on the analytical results, the modification rate of the lubricating oil can be estimated definitely. That is, the ratio of the peak heights of sample ④ to those of sample ② or the peak heights of sample ④ to those of sample ③ is determined, and is taken as the generation rate of the decomposition gases. Also, the rate of the viscosity change of the liquid fractions is determined by using the changes in molecular weight of the liquid fractions. The generation rate of the decomposition gases and the rate of the viscosity changed are used for the estimation of the modification rate of the lubricating oil.

By comparison with the recorded analytical-values of a sample practically used, the service life of the same kind of a sample can be estimated more definitely.

What is claimed is:

1. A method of pretreating and analyzing substances in an apparatus forming a closed flow path comprising a circulation pump, a gas sampling column, a sampling section, a vapor-liquid equilibrium section, a vapor-liquid separation section, piping and multi-way valves interconnecting said sections with said pump and said column, which comprises sampling a predetermined amount of a liquid sample in the sampling section; bringing the sample to a vapor-liquid equilibrium at a predetermined temperature and pressure by introducing a purge gas through one of said multi-way valves and by circulating the sample with the purge gas in the vapor-liquid equilibrium section; separating resultant gaseous and liquid fractions from each other in the vapor-liquid separation section while introducing the purge gas and the sample into said separation section, whereby the liquid fraction remains in said separation section; introducing the gaseous fraction into the gas sampling column; removing the gaseous fraction from said column and removing the liquid fraction from said vapor-liquid separation section and separately analyzing the gaseous fraction as a gas sample and the liquid fraction as a liquid sample quantitatively.

2. Apparatus for pretreating substances prior to analyzing the substances comprising a closed flow path of interconnected elements comprising piping, multi-way valves, a circulation pump, a gas sampling column, a vapor-liquid equilibrium section and a sampling section in which a liquid sample is initially collected, said sampling section along with a purge gas supply means being connected to an inlet of the vapor-liquid equilibrium section in which the sample with the purge gas is brought to a vapor-liquid equilibrium under conditions of temperature and pressure controlled to predetermined values by the pressure of the purge gas and by means for maintaining the apparatus at predetermined temperatures, a vapor-liquid separation section, within the vapor-liquid equilibrium section, in which gaseous and liquid fractions of the sample which are produced in the vapor-liquid equilibrium section are separated from each other in the presence of the purge gas; said separation section including a vapor-liquid separation vessel and means introducing the purge gas into said vapor-liquid separation vessel at a lower portion thereof so that a sample in said vessel is brought into contact with said purge gas thereby separating the sample into said gaseous and liquid fractions; said piping and said multi-way valves interconnecting said gas sampling column, said vapor-equilibrium section, said sampling section and the gas sampling column in series.

3. Apparatus according to claim 2, further comprising means for quantitatively analyzing the gaseous and liquid fractions; said piping, said multi-way valves and said circulation pump comprising first means for transferring the liquid sample from the sampling section to the vapor-liquid equilibrium section with said purge gas, said vapor-liquid equilibrium section including the vapor-liquid separation section for separating the gaseous fraction and the liquid fraction of the liquid sample from each other and second means for transferring the gaseous fraction of the liquid sample from the vapor-liquid separation section to the gas sampling column; means for introducing a carrier gas into said gas sampling column for removing the gaseous fraction and introducing said gaseous fraction into means for quantitatively analyzing the gaseous fraction; means for introducing a solvent for effecting dilution of the liquid fraction retained in the vapor-liquid separation section; and means for transferring the liquid fraction of the liquid sample from the vapor-liquid separation section with said solvent to means for effecting quantitative analysis of the liquid fraction.

* * * * *